United States Patent
Pacetti et al.

(10) Patent No.: US 10,441,448 B2
(45) Date of Patent: Oct. 15, 2019

(54) FLOW REGULATION VALVE FOR CONTROLLING INFLATION RATE OF A BALLOON DEPLOYING A SCAFFOLD

(71) Applicant: Abbott Cardiovascular Systems Inc., Santa Clara, CA (US)

(72) Inventors: Stephen D. Pacetti, San Jose, CA (US); Yunbing Wang, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 673 days.

(21) Appl. No.: 15/015,945

(22) Filed: Feb. 4, 2016

(65) Prior Publication Data

US 2016/0158046 A1 Jun. 9, 2016

Related U.S. Application Data (62) Division of application No. 13/471,263, filed on May 14, 2012, now Pat. No. 9,289,319.

(51) Int. Cl.
| | | |
|---|---|---|
| A61F 2/958 | (2013.01) | |
| A61M 25/10 | (2013.01) | |
| A61M 39/24 | (2006.01) | |
| A61M 5/168 | (2006.01) | |

(52) U.S. Cl.
CPC .......... *A61F 2/958* (2013.01); *A61M 25/104* (2013.01); *A61M 25/10184* (2013.11); *A61M 25/10185* (2013.11); *A61M 39/24* (2013.01); *A61M 5/16877* (2013.01); *A61M 2039/2413* (2013.01)

(58) Field of Classification Search
CPC . A61F 2/958; A61M 25/1018; A61M 25/104; A61M 25/10184; A61M 25/10185; A61M 39/24; A61M 2039/2413
See application file for complete search history.

(56) References Cited

U.S. PATENT DOCUMENTS

| | | | | |
|---|---|---|---|---|
| 3,795,246 A | * | 3/1974 | Sturgeon | .......... A61B 17/12109 604/907 |
| 4,429,856 A | * | 2/1984 | Jackson | ................ A61M 16/04 137/843 |
| 4,957,483 A | * | 9/1990 | Gonser | .................... A61C 1/18 251/149.7 |
| 5,437,632 A | * | 8/1995 | Engelson | .......... A61M 25/0045 604/523 |

(Continued)

FOREIGN PATENT DOCUMENTS

| | | |
|---|---|---|
| EP | 2 383 007 | 11/2011 |
| WO | WO 97/37714 | 10/1997 |

(Continued)

OTHER PUBLICATIONS

International Search Report and Written Opinion dated Oct. 21, 2013 in International Patent Application No. PCT/US2013/039980, 17 pages.

(Continued)

*Primary Examiner* — Julie A Szpira
(74) *Attorney, Agent, or Firm* — Squire Patton Boggs (US) LLP (57) ABSTRACT

An apparatus and method for controlling inflation pressure, pressurization rate, and volumetric flow rate of a balloon during deployment of a stent or scaffold is disclosed.

11 Claims, 7 Drawing Sheets

(56) References Cited

U.S. PATENT DOCUMENTS

| | | | |
|---|---|---|---|
| 5,514,110 A * | 5/1996 | Teh | A61M 5/16881 |
| | | | 137/517 |
| 5,893,868 A | 4/1999 | Hanson et al. | |
| 6,050,973 A * | 4/2000 | Duffy | A61M 25/104 |
| | | | 137/505.13 |
| 6,419,657 B1 * | 7/2002 | Pacetti | A61F 2/958 |
| | | | 137/513.3 |
| 2003/0078538 A1 | 4/2003 | Neale et al. | |
| 2004/0220522 A1 * | 11/2004 | Briscoe | A61M 25/0075 |
| | | | 604/99.04 |
| 2006/0118189 A1 * | 6/2006 | Tekulve | A61M 39/22 |
| | | | 137/846 |
| 2009/0254049 A1 | 10/2009 | Adams | |
| 2011/0288478 A1 * | 11/2011 | Ehrenreich | A61M 25/10181 |
| | | | 604/99.04 |

FOREIGN PATENT DOCUMENTS

| | | |
|---|---|---|
| WO | WO 2010/086476 | 8/2010 |
| WO | WO 2011/137372 | 11/2011 |

OTHER PUBLICATIONS

Office Action dated Aug. 18, 2016 in European Patent Application No. 13723645.1, 4 pages.
Office Action dated Jan. 24, 2017 in Japanese Patent Application No. 2015-512687, 6 pages.

* cited by examiner

FLOW REGULATION VALVE FOR CONTROLLING INFLATION RATE OF A BALLOON DEPLOYING A SCAFFOLD

This application is a division of application Ser. No. 13/471,263 which was filed May 14, 2012 and is incorporated by reference herein.

BACKGROUND OF THE INVENTION

Field of the Invention

This invention relates to a method and apparatus for deployment of a stent or scaffold in the treatment of coronary and peripheral artery disease.

Description of the State of the Art

This invention relates generally to methods of treatment with radially expandable endoprostheses that are adapted to be implanted in a bodily lumen. An "endoprosthesis" corresponds to an artificial device that is placed inside the body. A "lumen" refers to a cavity of a tubular organ such as a blood vessel. A scaffold is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent vasospasm and acute closure, as well as tack up dissections. Stents also reduce restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter so that they can be delivered to and deployed at a treatment site.

Stents are typically implanted by use of a catheter which is inserted at an easily accessible location and then advanced through the vasculature to the deployment site. The stent is initially maintained in a radially compressed or collapsed state to enable it to be maneuvered through a body lumen. Once in position, the stent is usually deployed either automatically by the removal of a restraint, actively by the inflation of a balloon about which the stent is carried on the deployment catheter, or both.

In reference to balloon expandable stents, the stent is mounted on and crimped to the balloon portion the catheter. The catheter is introduced transluminally with the stent mounted on the balloon and the stent and balloon are positioned at the location of a lesion. The balloon is then inflated to expand the stent to a larger diameter to implant it in the artery at the lesion. An optimal clinical outcome requires correct sizing and deployment of the stent.

An important aspect of stent deployment is the rapidity with which the stent is expanded. For balloon deployed stents, this is controlled by the balloon inflation rate. Inflation is usually achieved through manual inflation/deflation devices (indeflators) or an indeflator unit that possesses some automation.

Stents made from biostable or non-degradable materials, such as metals that do not corrode or have minimal corrosion during a patient's lifetime, have become the standard of care for percutaneous coronary intervention (PCI) as well as in peripheral applications, such as the superficial femoral artery (SFA). Such stents, especially antiproliferative drug coated stents, have been shown to be capable of preventing early and later recoil and restenosis.

It has been recognized for metal stents that slower inflation is better. During inflation, kinetic effects create non-equilibrium conditions. For example, the friction of the balloon against the stent is affected by inflation rate. A fast inflation/deflation cycle can result in higher levels of stent recoil. Inflation speed affects the uniformity of stent deployment along its length. Often, the distal and proximal ends of the balloon inflate first. A dumbbell or dog bone shape is created which exerts a net inward force on the stent. Consequently, fast stent inflation may lead to more stent shortening. Ideally, the stent is deployed uniformly, with an even spreading of the struts around the periphery. Fast deployment is believed to increase the likelihood of struts being clustered together in sections and over expanded in others.

Additionally, there are many potential reasons why inflation speed affects stent expansion. Catheter balloons can be folded in a non-uniform way. Balloon folds can get stuck or "caught" on stent struts. The lesion environment is rarely uniform, or with a perfectly concentric plaque. Lesions are typically eccentric, sometimes with fibrous or calcified focal regions. Consequently, the resistance to radial expansion of the balloon may be greater in certain directions resulting in an eccentric deployment. Lesion tissues can also have viscoelastic properties such that high inflation rates may result in more tissue damages versus slow stretching of the tissue. Lastly, in clinical practice, the process of stent implantation can become routine. Such familiarity often leads to shorter procedural times which tend to beneficial for the patient except for steps, such as stent inflation, where faster is not always better.

In order to effect healing of a diseased blood vessel, the presence of the stent is necessary only for a limited period of time, as the artery undergoes physiological remodeling over time after deployment. A bioresorbable stent or scaffold obviates the permanent metal implant in vessel, allowing late expansive luminal and vessel remodeling, leaving only healed native vessel tissue after the full resorption of the scaffold. Stents fabricated from bioresorbable, biodegradable, bioabsorbable, and/or bioerodible materials such as bioabsorbable polymers can be designed to completely absorb only after or some time after the clinical need for them has ended. Some or all of the reasons for a slower inflation rate for metallic stent may also apply to balloon expandable polymer stents or scaffolds. Most importantly, due to the viscoelastic properties of high molecular weight polymers, these materials tend to become more rigid when deformed at a faster rate, which makes it critical to control the inflation rate of a polymeric stent to prevent any potential formation of cracks and broken struts.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Embodiments of the present invention include a flow regulator for regulating flow of an inflation fluid to a balloon catheter, comprising: a valve body enclosing a control chamber comprising a passageway for fluid flow; a distal end of the valve body with a distal flow orifice for connection with the balloon catheter, a proximal end of the valve body with a proximal flow orifice for connection with a catheter in fluid communication an inflation device, a slidable restrictor body positioned within the control chamber to allow fluid flow distally or proximally through the restrictor body; a valve seat positioned distal to the restrictor body comprising a valve seat orifice which allows fluid to flow out of the distal flow orifice; wherein the slidable restrictor body slide is operable to slide distally in response to fluid flow in the distal direction toward the valve seat during inflation of the balloon, wherein as a distal end of the restrictor body approaches the valve seat they cooperate to increase restriction to fluid flow which controls the pressurization rate of the balloon to within a specified range.

Embodiments of the present invention include a flow regulator for regulating flow of an inflation fluid to a balloon catheter, comprising: a valve body enclosing a control chamber comprising a passageway for fluid flow; a distal end of the valve body with a distal flow orifice for connection with the balloon catheter, a proximal end of the valve body with a proximal flow orifice for connection with a catheter in fluid communication an inflation device, a flexible restrictor membrane positioned within the control chamber comprising an opening which allows fluid to flow distally or proximally through the membrane; a valve seat positioned within the control chamber distal to the membrane comprising an opening for fluid to flow distally and proximally; wherein the membrane is operable to flex distally in response to fluid flow in the distal direction toward the valve seat during inflation of the balloon, wherein as the membrane flexes toward the valve seat restriction to fluid flow increases which controls the pressurization rate of the balloon to within a specified range.

Embodiments of the present invention include a method for deployment of a stent comprising: delivering a scaffold crimped over a delivery balloon, wherein the balloon is connected to an inflation system comprising a valve in a flow path of fluid including a slidable element that slides in a direction of fluid flow; and flowing the fluid through the inflation system to inflate the balloon and expand the scaffold, wherein the flow induces sliding of the slidable element which allows the slidable element to increase resistance to flow of the fluid to the balloon which controls an inflation rate of the balloon within a selected range.

Embodiments of the present invention include a method for deployment of a stent comprising: delivering a scaffold crimped over a delivery balloon, wherein the balloon is connected to an inflation system comprising a valve in a flow path of fluid including a flexible membrane that deforms in a direction of fluid flow; and flowing the fluid through the inflation system to inflate the balloon and expand the scaffold, wherein the flow induces deformation of the membrane which allows the membrane to increase resistance to flow of fluid to the balloon which controls an inflation rate of the balloon to a selected range.

Embodiments of the present invention include a flow regulator for regulating flow of an inflation fluid to a balloon catheter, comprising: a valve body enclosing a control chamber comprising a passageway for fluid flow; a distal end of the valve body with a distal flow orifice for connection with the balloon catheter, a proximal end of the valve body with a proximal flow orifice for connection with a catheter in fluid communication an inflation device, a slidable restrictor body positioned within the control chamber to allow fluid flow distally or proximally through the restrictor body; and a valve seat extending proximally from a distal end of the valve body, wherein the valve seat comprises a valve seat orifice at its distal end which allows fluid to flow out of the distal flow orifice, wherein the slidable restrictor body is operable to slide distally in response to fluid flow in the distal direction during inflation of the balloon, wherein as a proximal end of the restrictor body approaches the valve seat orifice, the proximal end of the restrictor body and the valve seat cooperates to increase restriction to fluid flow which controls the pressurization rate of the balloon to within a specified range.

DETAILED DESCRIPTION OF THE INVENTION

Generally, the present invention includes delivery systems and methods for delivery of stents in lumens or vessels. In particular, the present invention relates to apparatuses and methods for controlling the inflation rate of a balloon that deploys a stent. More specifically, the apparatuses and accompanying method provide a flow regulator for regulating flow of an inflation fluid in a stent delivery balloon catheter.

The present invention incorporates a regulator valve in the flow path of an inflation lumen between a pressurized fluid source and a balloon. The valve regulates the flow of liquid used to inflate the balloon. The valve is adapted to restrict flow and to respond to increases in pressure which may be applied by an inflation device to assure a desired inflation rate. During deflation, the valve is designed to offer little or no resistance to fluid evacuation, allowing the balloon to be deflated quickly.

In operation, the embodiments of the flow regulator valve of the present invention may be connected in line with a deployment balloon to be utilized in carrying a scaffold into position and deployment thereof. In some configurations, the regulator valve could be incorporated directly in the proximal hub of the balloon catheter. In still others, the regulator valve could be constructed as a separate component which is attachable to a balloon delivery catheter or inflation pump. The invention can be incorporated into an inflation device as well.

The methods and systems are particularly applicable to, though not limited to, deployment of bioresorbable scaffolds. Such scaffolds can include a support structure in the form of a scaffold made of a material that is bioresorbable, for example, a bioresorbable polymer such as a lactide-based polymer. The scaffold is designed to completely resorb away from an implant site after treatment of an artery is completed. The scaffold can further include a drug, such as an antiproliferative or anti-inflammatory agent. A polymer coating disposed over the scaffold can include the drug which is released from the coating after implantation of the stent. The polymer of the coating may also be bioresorbable.

The present invention, however, is not limited for use with bioresorbable scaffolds or even stents. It is also applicable to various polymeric scaffolds/stents, metallic stents, stent-grafts, and generally tubular medical devices in the treatment of bodily lumens where it is desirable to control the expansion of such devices in the lumens.

A stent or scaffold can include a plurality of cylindrical rings connected or coupled with linking elements. For example, the rings may have an undulating sinusoidal structure. When deployed in a section of a vessel, the cylindrical rings are load bearing and support the vessel wall at an expanded diameter or a diameter range due to cyclical forces in the vessel. Load bearing refers to supporting of the load imposed by radially inward directed forces. Structural elements, such as the linking elements or struts, are generally non-load bearing, serving to maintain connectivity between the rings. For example, a stent may include a scaffold composed of a pattern or network of interconnecting structural elements or struts.

Figure 1:
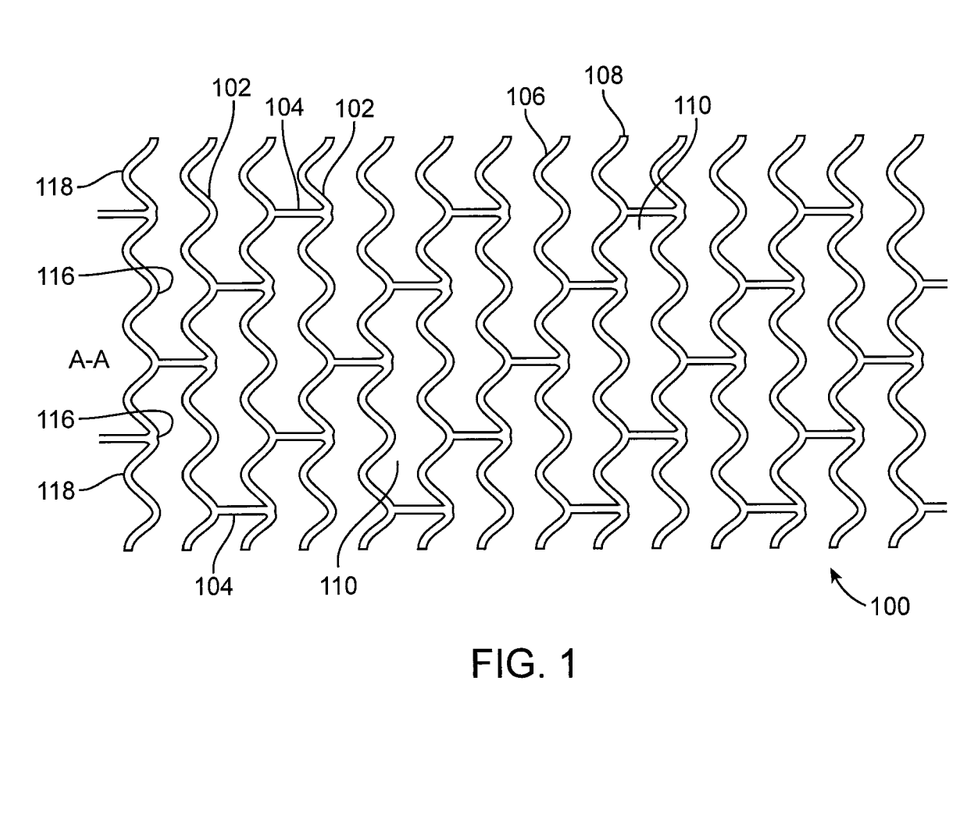
FIG. 1 illustrates a portion of an exemplary prior art stent or scaffold pattern shown in a flattened view.

FIG. 1 illustrates a portion of an exemplary stent or scaffold pattern 100 shown in a flattened view. The pattern 100 of FIG. 1 represents a tubular scaffold structure so that a cylindrical axis A-A is parallel to the central or longitudinal axis of the scaffold. FIG. 1 shows the scaffold in a state prior to crimping or after deployment. Pattern 100 is composed of a plurality of ring struts 102 and link struts 104. The ring struts 102 form a plurality of cylindrical rings, for example, rings 106 and 108, arranged about the cylindrical axis A-A. The rings have an undulating or sinusoidal structure with alternating crests or peaks 116 and troughs or valleys 118. The rings are connected by the link struts 104. The scaffold has an open framework of struts and links that define a generally tubular body with gaps 110 in the body defined by rings and struts. A cylindrical tube may be formed into this open framework of struts and links by a laser cutting device that cuts such a pattern into a thin-walled tube that may initially have no gaps in the tube wall.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching.

Prior to insertion in the body, a bioresorbable scaffold, like a metallic stent, is tightly compressed onto a balloon. Plastic deformation of the crimped scaffold induced by the crimping process helps retain that the scaffold on the balloon. Once it is positioned at an implant site, the bioresorbable scaffold is expanded by the balloon. The expansion of the scaffold induces areas of plastic stress in the bioresorbable material to cause the scaffold to achieve and maintain the appropriate diameter on deployment.

An exemplary scaffold for coronary applications has the stent pattern described in US 2010/0004735. Other examples of stent patterns suitable for bioresorbable polymers are found in US 2008/0275537, specifically, the pattern depicted in FIG. 15.

A stent or scaffold delivery system includes a hollow catheter with an inflation lumen. A proximal end of the catheter has a catheter hub that connects to an inflation device, which can be an indeflator. The distal end of the catheter is connected to a stent-balloon assembly. As indicated above, prior to insertion into a patient, the balloon is in a deflated state in a low profile configuration with the stent crimped thereon. The inflation device has access to a source of inflation fluid.

Once the stent-balloon assembly is positioned at an implant site, the inflation device injects inflation fluid into the inflation lumen of the catheter. The fluid flows through the inflation lumen into the balloon. As fluid is injected into the inflation lumen and the balloon, the pressure therein increases with time, causing the balloon to inflate and expand the stent. Once the stent is fully expanded, the balloon is deflated and withdrawn from the implant site, leaving the stent at the implant site apposed against the vessel wall. The balloon is deflated by a negative pressure in the inflation lumen imposed by the inflation device which withdraws inflation fluid from the balloon.

An exemplary inflation device is the 20/30 Indeflator Inflation Device made by Abbott Vascular-Cardiac Therapies of Temecula, Calif., USA. The indeflator includes a pressure injector at a proximal end and an exit port at a distal end at the tip of a flexible tube that connects to a catheter hub. The inflation device has a chamber for holding inflation fluid for injecting into the catheter. The inflation device has a pressure gauge that measures the pressure of the injected inflation fluid. A typical inflation device has a handle for manual control by a physician of injection of inflation fluid. The handle is turned which moves a piston to inject inflation fluid which increases the pressure of the inflation fluid in the catheter and balloon. The rate that the handle is turned determines the injection rate and thus the rate of pressure increase.

The inflation fluid itself may assist the physician in visualizing the catheter and balloon during delivery. A fluid that is visible to an imaging technique, such as x-ray fluoroscopy or magnetic resonance imaging (MRI), may be used to inflate a balloon. Such fluids are referred to as contrast agents. Thus, a contrast agent can include a radiopaque agent or a magnetic resonance imaging agent. "Radiopaque" refers to the ability of a substance to absorb x-rays. An MRI contrast agent alters the relaxation behavior of hydrogen nuclei or has a magnetic susceptibility that allows it to be visible with MRI.

Polymers that are stiff or rigid under conditions within a human body are promising for use as a scaffold material. Specifically, polymers that have a glass transition temperature (Tg) sufficiently above human body temperature, which is approximately 37° C., should be stiff or rigid upon implantation. For example, poly(L-lactide) (PLLA) or PLLA-based polymers have both relatively high strength and stiffness at human body temperature.

The advantages of a slower inflation rate during deployment for metallic stents may also apply to bioresorbable scaffolds. The inventors have hypothesized that an additional rationale for a slower inflation rate for polymer scaffolds or stents is that potential for damage (e.g., fracture, breaking of struts) to a polymer scaffold increases at higher inflation rate. In short, the susceptibility of a polymer scaffold to damage may be a function of inflation rate. The potential for damage to a polymer scaffold at higher inflation rates may be greater than for metal stents.

Certain polymers may have suitable strength and stiffness properties, however, such polymers tend to have lower ultimate elongation (i.e., elongation at break) or ductility than metals. This potential weakness can be mitigated by a combination of scaffold design and polymer processing. Also, polymers (e.g., PLLA) exhibit viscoelastic behavior where the accumulated stress in the material is a function of the strain history, including the strain rate. Therefore, bioresorbable polymer scaffolds may be more susceptible to strut material damage as the inflation or expansion rate increases.

More specifically, for the bioresorbable scaffold disclosed above, the inventors have observed that deployment begins at the ends of the stent or scaffold and propagates toward the middle. The reasons for most balloon expandable stents to deploy first at the ends is the presence of balloon tapers, and the fact that the stent margins define discontinuities where the stent is easier to deform. This deployment pattern of first at the ends is often referred to as "dogboning." After the ends have partially inflated, the stent or scaffold deploys from the ends towards the center. This has the appearance of two expansion waves propagating towards each other. The inventors hypothesize that a high rate of crest opening in the middle increases risk of premature fractures. The inventors further hypothesize that employing directional control on inflation will drive overall more consistent deployment speed and eliminate the potential for premature fractures.

The inventors have tested their hypothesis that bioresorbable polymer scaffolds may be more susceptible to damage at higher inflation rates. Bench tests on bioresorbable scaffolds were performed to evaluate the effect of inflation rate on damage. The scaffolds used in the test have a pattern similar to that shown in FIG. 15 of US 2008/0275537. The scaffolds are 3 mm in diameter and 18 mm long. The thickness and width of the scaffold struts is about 150 microns. Detailed discussion of the manufacturing process of the bioresorbable scaffold can be found elsewhere, e.g., U.S. Patent Publication No. 2007/0283552.

As a more controlled surrogate for balloon inflation, the test involved moving two parallel pins apart that are disposed within and along the axis of a scaffold. As the pins were extended or moved apart, the load applied to the scaffold was measured as a function of extension of the pins. Four runs were performed at different rates to simulate different inflation rates. A discontinuity in the load vs. extension curves indicates the extension at which failure of ring struts occur. Table 1 below shows the extension at which ring struts fractured for each run. The data is Table 1 shows that as the extension rate increases, the extension at break or fracture of the scaffold decreases. These results imply that damage to a polymer scaffold depends on the inflation rate of a balloon during deployment. Specifically, it is expected that damage to scaffold will occur at lower deployment diameters as the inflation rate increases.

TABLE 1

Extension at fracture for polymer scaffolds for four runs with different extension rates.

| Run | Rate (mm/min) | Extension at All Ring PDTF ID* (mm) |
|---|---|---|
| 1 | 0.254 | 6.522 |
| 2 | 2.54 | 6.073 |
| 3 | 25.4 | 5.527 |
| 4 | 254 | 5.325 |

*Post deployment to fracture inside diameter - deformation of scaffold is continued until broken.

It is believed that control of the inflation rate or average inflation rate below a certain value for at least a portion of the deployment process will prevent or mitigate scaffold damage during deployment, and ultimately allow for higher degrees of expansion. The inflation rate can be expressed in terms of the pressure of the inflation fluid within the inflation lumen and the balloon, for example, in psi/sec. While this inflation rate may be readily measured with a manual indeflator that contains a pressure gauge calibrated to psi, a more correct measure of inflation rate is the volumetric flow rate which has units of volume/time.

Imposition of a maximum inflation rate might rely on physician training to achieve compliance. However, there is no guarantee that this inflation rate will be followed in clinical practice. Physicians are accustomed to stent devices that, while they have specific inflation rates dictated in the Instructions For Use, do not experience undue consequences if they are inflated faster than the specified inflation rates. For example, although there are reasons for a slower inflation rate for metals, the stress behavior of the material is not a strong function of strain rate, so stent damage is not as significant a concern.

Interventional procedures sometimes require a fast inflation of a balloon, stent, or scaffold. One reason would be the presence of a coronary perforation. Balloons by themselves, or balloons with scaffolds, are inflated rapidly to hold perforations closed and, hopefully, seal them. The patient may be experiencing other forms of duress such as ischemia induced angina, tachycardia, of fibrillation which pushes the physician to perform the procedure rapidly. Thus, there is a need for systems, and methods for control of scaffold inflation rate, that do not rely on manual physician adjustment.

Physician training may be used to achieve compliance of a low inflation rate, such as 6 psi/sec inflation rate. However, there is no guarantee that this inflation rate will be followed in clinical practice. Physicians are accustomed to current stent devices that, while they have specific inflation rates dictated in their respective Instructions for Use (IFU), do not experience undue consequences if they are inflated quickly. For metals, the stress behavior of the material is not a strong function of strain rate, unlike polymers. Moreover, a variety of indeflator devices are used in the marketplace to control the inflation rate and each require a different style of physical manipulation for each indeflator. For example, some indeflators require turning a T-shaped handle while others have the physician turning a round knob. There is also no standardization on the piston size or thread pitch used to move the piston. Consequently, the volume of inflation fluid displaced by one rotation is not necessarily the same between different models of manual indeflators.

Further complicating matters, the speed that the indeflator knob has to be turned to achieve a specified low inflation rate depends on balloon size. For example, for a 28 mm balloon, the indeflator knob is turned faster for a 6 psi/sec rate than for an 8 mm balloon as the 8 mm scaffold has a smaller volume balloon.

Schemes to control the inflation rate are preferably modifications of the balloon delivery catheter that would work with any indeflator. One such scheme is a capillary type of restrictor which is a small diameter tube that is placed inside the catheter hub in the balloon inflation flow path. However, there are several disadvantages of a capillary restrictor.

First, the restriction to contrast flow through a capillary restrictor is symmetrical meaning the balloon will inflate slowly and also deflate slowly. As pressure drops as high as 16 atm can be applied to the capillary restrictor, this dictates the diameter of the restrictor to comply with a low inflation rate such as 6 psi/sec. However, the pressure drop to deflate the balloon is no more than atmospheric pressure plus systolic pressure with a vacuum applied at the catheter hub. This pressure difference is no more than 1.5 atm leading to a deflation rate of the balloon that will be very slow.

An important performance attribute for any dilatation catheter is the deflation rate. Physicians want it to be fast to shorten total procedure time and to hasten moving on to the next step in the procedure. Also, while the balloon is inflated, the blood flow through the vessel is cut-off which essentially creates a temporary myocardial infarction. During balloon inflation, patients often experience chest pain. Consequently, rapid balloon deflation is a clinical requirement.

Second, a simple capillary restrictor can be overpowered by aggressive indeflator use. The flow through the capillary restrictor is proportional to the pressure applied. If the pressure upstream to the capillary restrictor is raised to 20 atm, the flow will exceed the targeted low inflation rate limit such as 6 psi/sec if the restrictor was designed to control the flow with a 10 atm pressure head.

Embodiments of the flow regulating valves of the present invention have the following desirable properties. First, the valve regulates the balloon inflation to be a target inflation rate or less than a selected low inflation rate, for example, 6 psi/sec, for any size balloon.

Second, the valve maintains the selected inflation rate independent of the applied pressure by the indeflator. In other words, the regulating valve would respond to the applied pressure to increase resistance to flow at higher applied pressures, and decrease resistance to flow at lower applied pressures.

Third, the flow regulating valve can offer resistance to flow the same or approximately the same as a length of catheter with no valve during balloon deflation.

Fourth, the flow regulating valve can optionally be present during balloon leak testing and offer no impediments to the test.

Fifth, the flow regulating valve can be small, fit within the catheter hub, and not require any redesign, or enlargement, of the package used to store a stent, balloon, and catheter assembly.

Sixth, the flow regulating valve may be tunable, or adjustable, to function properly with the first through fifth properties with different size balloons.

Seventh, the flow regulating valve is designed such that the valve controls the inflation rate as desired (e.g., the first property above) even after a terminal sterilization process, such as electron beam (e-beam) sterilization. The valve components can be made of materials that whose properties are changed by e-beam exposure. Therefore, the valves should be designed to take into account such exposure during sterilization.

Designing a valve with the first and second properties requires a determination of the volumetric flow rate that corresponds with a selected low inflation rate. To maintain the low inflation rate, the indeflator handle needs to be turned faster for a 28 mm balloon versus an 8 mm balloon. A hydraulic burst leak tester (HBLT) can be programmed to achieve a selected inflation rate. An HBLT can be obtained from Crescent Design of San Diego, Calif.

Figure 2:
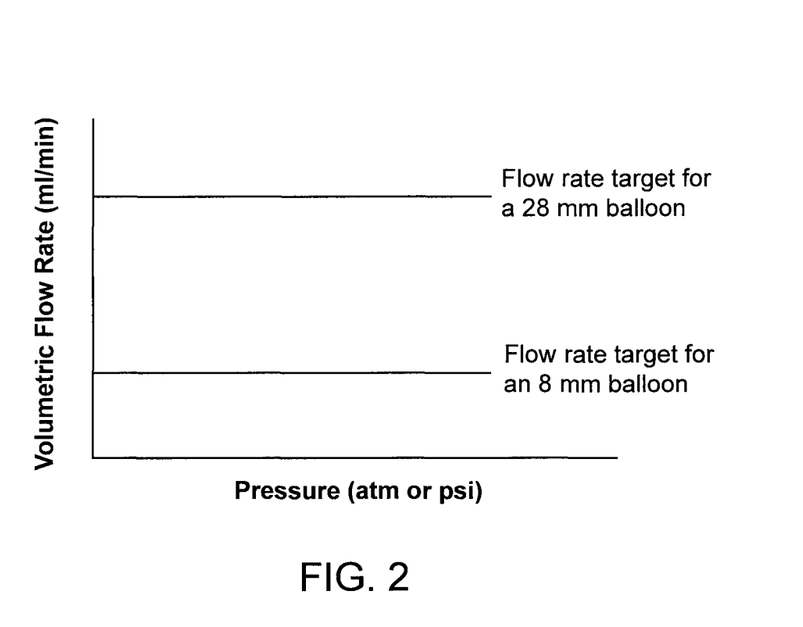
FIG. 2 depicts a flow rate versus pressure of inflation fluid.

The actual volumetric flow rate for different sized balloons that corresponds to selected low inflation rate can be obtained from the HBLT. For a balloon, the volume is given by $V=2\pi LR$ where R and L are the balloon radius and length, respectively. The first derivative of this equation with time gives:

$$dV/dt=2\pi L\ dR/dt,$$

which is the volumetric flow rate (Q). dR/dt is the change in radius of the scaffold with time, the quantity to be controlled, and is directly proportional to the volumetric flow rate Q. Therefore, for a valve to control the dR/dt, the valve should hold Q constant independent of the pressure applied to the valve. A test system for designing a flow regulating valve cannot rely solely on the indeflator pressure gauge. The test system should apply a known pressure of fluid to the valve and measure the resulting volumetric flow rate. The flow regulating valve should ideally generate a volumetric flow rate versus pressure curve as shown in FIG. 2. In actuality, the curve would not be a perfectly straight line but would have the volumetric flow rate decrease at very low pressures, and intersect the origin at zero applied pressure. In a test system, and in actual use, the applied pressure is the independent variable and the volumetric flow rate is the dependent variable.

Methods for deployment of a stent using embodiments of the inventive flow regulator valves include injecting an inflation fluid from a fluid source such an indeflator into an inflation lumen of a catheter in fluid communication with the delivery balloon. The catheter includes the fluid regulator valve in a path of the inflation fluid between the fluid source and the balloon. The valve maintains a pressurization rate of the inflation fluid within a specified range which controls the volumetric flow rate and, consequently, the inflation rate of the balloon.

A first set of inventive embodiments of a flow regulator for regulating flow of an inflation fluid to a balloon catheter includes a valve body enclosing a control chamber, a slidable restrictor body positioned within the control chamber, and a valve seat positioned within the control chamber distal to the valve body. The control chamber includes a passageway for fluid flow.

A proximal end of the valve body has a proximal flow orifice for connection with a catheter in fluid communication with an inflation device. A distal end of the valve body has a distal flow orifice for connection with the balloon catheter.

The slidable restrictor body is positioned within the control chamber around a section of the passageway which allows fluid flow distally or proximally through the section. The valve seat positioned distal to the restrictor body includes a valve seat orifice which allows fluid to flow out to the distal flow orifice. The valve can further incorporate a biasing element that applies a biasing force that opposes distal sliding of the restrictor body.

The inflation fluid flows distally during balloon inflation and proximally during deflation. The slidable restrictor body slide is operable to slide distally in response to fluid flow in the distal direction toward the valve seat during inflation of the balloon. As a proximal end of the restrictor body approaches the valve seat they cooperate to increase restriction to fluid flow which controls the pressurization rate of the balloon to within a specified range. The slidable restrictor body is further operable to slide proximally in response to fluid flow in the proximal direction during deflation of the balloon without increasing restriction of the proximal fluid flow.

An exemplary embodiment of this first set of embodiments of a flow regulator valve is shown in FIGS. 3, 4A-C, and 5-7.

Figure 3:
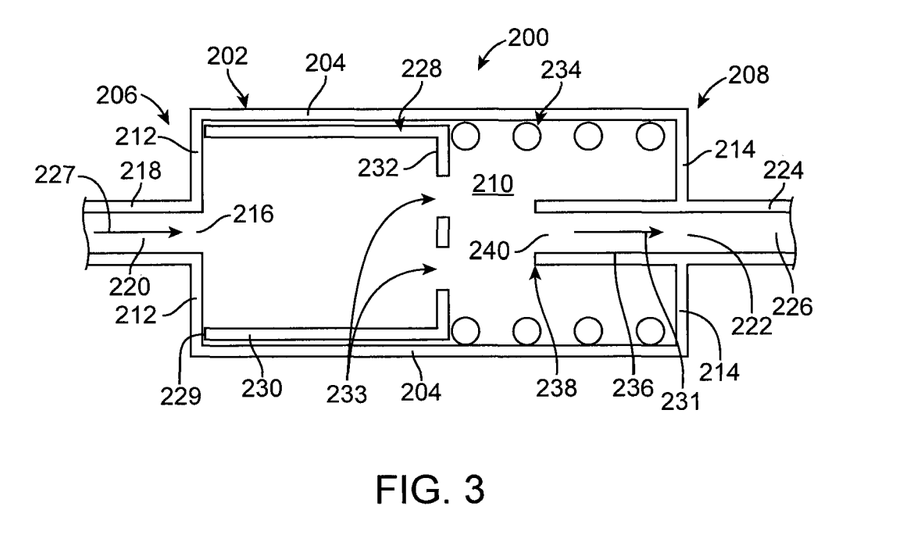
FIG. 3 depicts a longitudinal cross-section of a flow regulating valve including a valve body, cylindrical slide, and spring.

FIG. 3 depicts a longitudinal cross section of a valve 200 which includes a cylindrical valve body 202. Valve body 202 is formed of a cylindrical wall 204 that encloses a control volume 210 that includes a passage way between a proximal end 206 to a distal end 208 of valve 200. Valve body 202 further includes proximal wall 212 and distal wall 214 at the respective ends of cylindrical valve body 202.

Valve body 202 further includes a proximal orifice 216 in proximal wall 212 that is in fluid communication with a fluid source such as an indeflator (not shown). Valve body 202 is connected to a proximal catheter section 218 with an inflation lumen 220 that leads into proximal orifice 216.

At distal end 208, valve body 202 has a distal orifice 222 in distal wall 214 that is in fluid communication with a delivery balloon (not shown). Valve body 202 is connected to a distal catheter section 224 with an inflation lumen 226 that leads into distal orifice 222.

A cylindrical slide 228 is positioned within control volume 210 of valve body 202. Slide 228 has cylindrical walls 230 that enclose a passage way for flow of inflation fluid through valve body 202. Slide 228 further includes a distal wall 232 with two slide openings 233 which allow flow of inflation fluid distally or proximally. Slide 228 is positioned such that its cylindrical axis coincides with valve body 202. Slide 228 is slidable distally or proximally within valve body 202. Slide 228 has a proximal edge 229 which when abutting against inner surface of distal wall 212, prevents further proximal sliding of slide 228.

The outer diameter of slide 228 is close to or equal to the inner diameter of valve body 202. For example, the ratio of outer diameter of slide 228 and the inner diameter of valve body 202 is between 0.9 and 1 or between 0.9 and 0.99. In the configuration shown in FIG. 3, slide 228 is in the proximal-most position.

Valve 200 further includes a spring 234 positioned within control volume 210 between wall 232 of slide 228 and an inner surface of distal wall 214 of valve body 202. Spring 234 applies a proximally directed compression force that opposes the distal sliding of slide 228. In the configuration of FIG. 3, spring 234 is in a minimum or zero force state.

Valve 200 further includes a tubular valve seat 236 which extends proximally from distal wall 214 into control volume 210 to a valve seat edge 238. Valve seat 236 has a valve seat opening 240 for inflation fluid to flow to distal orifice 222. Valve seat 236 can be a rigid plastic or metal tube with a lumen for fluid flow.

In FIG. 3, the valve is in its rest configuration or the configuration with a low flow rate which does not cause distal sliding of slide 228. Such a configuration may correspond to an inflation pressure between 1 and 18 atm. The upper limit of the inflation pressure may also be 8 atm or 24 atm. During balloon inflation, inflation fluid from the fluid source flows through inflation lumen 220 and proximal orifice 216, as shown by arrow 227, into control volume 210 of valve body 202. The inflation fluid flows through the volume enclosed by slide 228 and through slide openings 233. The inflation fluid then flows into valve seat 236 through valve seat opening 240 and then through distal orifice 222 into distal catheter section 224, as shown by arrow 231.

Figures 4A, 4B:
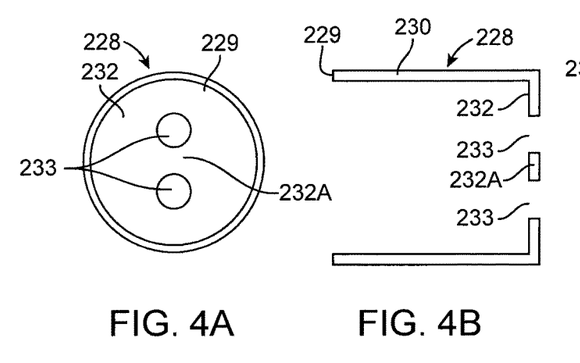
FIG. 4A is a proximal view of a cross-section of the slide of the valve from FIG. 3.
FIG. 4B is a longitudinal cross-section of the slide of the valve from FIG. 3.
Figure 4C:
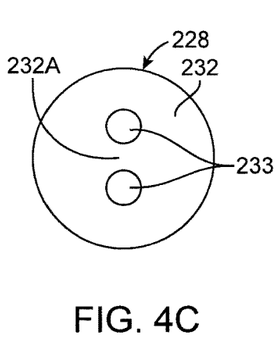
FIG. 4C is a distal view of a cross-section of the slide of the valve from FIG. 3.

FIGS. 4A-C depicts three cross-sectional views of cylindrical slide 228. FIG. 4A is the view from the proximal side or left directed side from looking inside slide 228. FIG. 4A depicts a proximal surface of distal wall 232, distal openings 233 in distal wall 232, and proximal edge 229. FIG. 4B depicts the longitudinal cross-section of slide 228. FIG. 4C shows a distal surface of distal wall 232 of slide 228 and distal openings 233.

As shown above, slide 228 is shaped like a piston with the two openings or holes 233 therein. As fluid flows distally or from left to right during balloon inflation, the inflation fluid passes through the two holes 233. The holes are positioned symmetrically, i.e., equidistant from the center of the surface of distal wall 232 and proximal edge 229 (or inner surface of wall 230). The symmetric positioning of holes 233 allows the slide to move freely along the inner surface of wall 204 of valve body 202 without binding against the walls. This is due to the symmetry of the frictional forces applied to the slide by the fluid flow. Other configurations and numbers of holes are possible.

As the flow rate increases during balloon inflation, pressure increases on the upstream side of the cylindrical slide 228. The pressure of the fluid applies a force on the proximal surface of distal wall 232. This force or pressure causes slide 228 to move to the right, compressing spring 234.

Figure 5:
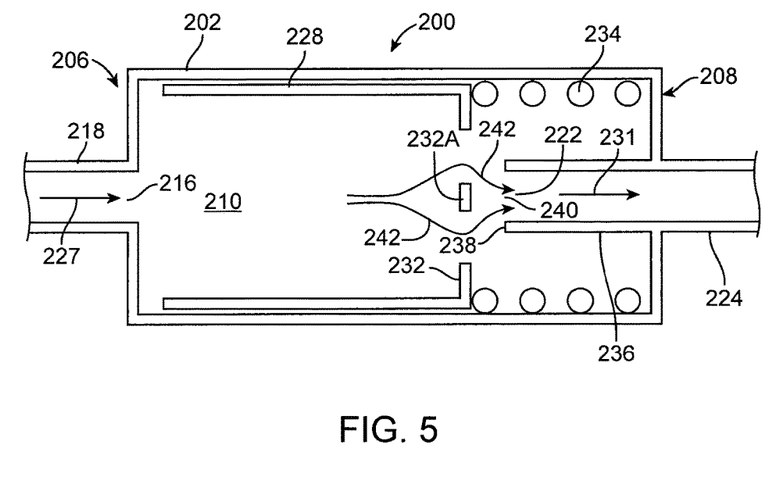
FIG. 5 depicts the valve of FIG. 3 with the cylindrical slide moved to distally and restricting flow.

As slide 228 moves to the right, distal wall 232 becomes close enough to valve seat edge 238 that the restriction to fluid flow is increased. FIG. 5 depicts a configuration in which slide 228 has slid to the right and restriction to fluid flow increases. As shown in FIG. 5, the restriction in the fluid flow arises due to the close proximity of section 232A of wall 232 to valve seat opening 240. A shown by arrows 242, section 232A interferes with the direct flow of fluid into valve seat opening 240. Fluid must flow around section 232A to enter valve seat opening 240. The gap between section 232A and valve seat edge 238 of valve seat 236 is the area available for flow into valve seat opening 240. As slide 228 slides distally, the gap because smaller, reducing flow area, thus increasing restriction to flow. This increase in restriction to flow increases the pressure drop across the valve. It is this decrease in effective gap or orifice size for fluid flow that leads to an increase in pressure drop across the valve, which in turn keeps the flow constant despite a higher applied pressure.

If the pressure across the valve is raised further, then the pressure drop across slide 228 will increase causing it to move further to the right. When the pressure is sufficiently high, valve 200 can attain a closed configuration or state such that slide 228 moves far enough to the right that proximal wall 232 engages or contacts valve seat edge 238 of valve seat 236, which is the furthest that slide 228 can slide to the right.

Figure 6:
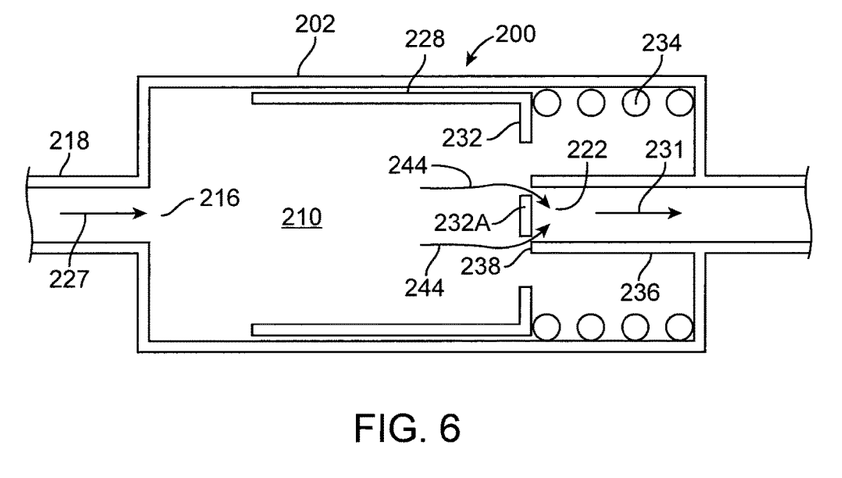
FIG. 6 depicts the valve of FIG. 3 with the cylindrical slide moved to the maximum distal position which is the maximal restriction of flow.

FIG. 6 depicts a closed configuration of valve 200 in which slide 228 is moved to a right-most or maximal distal position. In this closed configuration of valve 200, proximal wall 232 engages or contacts valve seat edge 238 of valve seat 236. In the closed configuration, the area available for fluid flow of distal opening 240 of valve seat 236 is a minimum resulting in a maximal restriction of flow since the gap between proximal wall 232 and valve seat edge 238 is at a minimum. Section 232A of wall 232 blocks most of the cross-sectional area of distal opening 240. As shown by arrows 244, fluid flows into two small openings where section 232A does not block distal opening 240. As shown, spring 234 is fully compressed.

Figure 7:
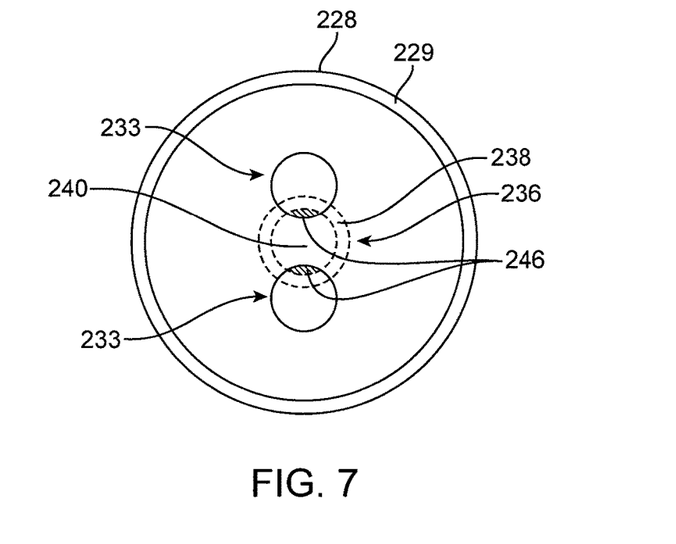
FIG. 7 depicts the cylindrical slide and valve seat from FIG. 6 viewed from a distal position.

FIG. 7 depicts cylindrical slide 228 in the configuration of FIG. 6 viewed from the left or from a distal position. Proximal edge 238 of valve seat 236 is shown in phantom as dashed lines. As shown in FIG. 7, openings 233 in wall 232 of slide 228 partially overlap with distal opening 240 of valve seat 236 to form two small openings 246. Therefore, even when closed all of the way, some fluid can still pass through the flow regulating valve, as shown by arrows 244.

It is important that the valve does not completely close, even at high applied pressure. This is to avoid the valve completely closing off which prevents additional inflation fluid from being administered unless the indeflator pressure is released.

As indicated in FIGS. 6 and 7, two very small flow paths 244 through openings 246 are shown. These openings may be sized so that even if the indeflator were suddenly ramped to a high pressure such as above 12, 14, or 18 atm, the scaffold would be inflated at the desired rate. However, the physician would ideally not raise the pressure above the value targeted for the selected scaffold diameter.

The configuration of openings shown in the surface of slide 228 is exemplary and other configurations are possible. In general, the surface of the slides includes openings. The openings are aligned with a valve seat opening such that when the surface contacts the valve seat edge, the valve seat opening is partially, but not completely blocked by a surface of the slide surface. At least a portion of the slide openings overlap the valve seat opening upon contact. The overlapping portions are an opening(s) for fluid flow when valve is completely closed.

Another exemplary configuration for the cylindrical slide is one small opening in the center and the two holes set off to the side. The small hole in the center would be the high pressure bleed hole. This configuration would be less sensitive to alignment as the two holes set off to the side (233 for example) would not overlap at all with valve seat edge 238. With this design, should the slide shift from side to side within the valve body due to looser tolerances, the fluid flow paths through holes in wall 232 would be unaffected.

When the balloon is deflated, fluid flow is reversed, causing slide 228 to move completely to the left with no increase in resistance to fluid flow caused by interference of flow due to close proximity of slide 228 and valve seat 236. The resistance to flow due to the valve in this configuration may be the same or approximately the same as. Slide 228 returns to the rest position depicted in FIG. 3 with proximal edge 229 abutting inner surface 212 of valve body 202.

Several other configurations of valve 200 are possible. The valve body and slide may not be cylindrical in cross section, The valve body and restrictor body may be conduits with other cross sectional shapes such as square or rectangular.

In other embodiments, the orientation of cylindrical slide could conceivably be reversed with wall 232 being situated at the proximal end of the slide. In this case, the valve seat 236 would need to be extended longer in the proximal direction in order to appropriately engage section 232A of wall 232. Also, in this case, spring 234 would be situated inside the cylindrical slide, but would still have its distal end abutting distal wall 214.

In yet another embodiment, the position of the holes for fluid flow, 233, and the valve seat 236 would be switched. The valve seat would be on cylindrical slide as a tube extending from wall 232. Holes 233 would then be positioned in distal wall 214. This configuration has the challenge that the region of greatest pressure drop is not necessarily associated with the cylindrical slide, and this may alter the valve sensitivity.

Valve 200 may be present in the catheter during the manufacturing process of the scaffold-balloon-catheter assembly. For example, if the balloon is pressurized with air during crimping, the valve would not activate as the low viscosity of air will not move the slide. Similarly, the catheter may be leak tested with the valve in place as air will not activate the valve.

In this first set of embodiments of a flow regulator valve, there are many parameters that determine the valve performance. These include the valve body diameter, valve body length, slide diameter, slide length, spring constant, slide opening(s) size, slide opening(s) position(s), and slide opening(s) spacing.

To design the valve, the basic shape can be input into a computational fluid mechanics software. Inflation media has a viscosity in the range of 2-4 cP and can be modeled as a Newtonian fluid. Modeling the valve behavior on the computer allows an approximate design to be established. Then, prototype valves could be machined with bodies of a metal such as aluminum, slides of metal or rigid plastic such as Delrin (polyoxymethylene) made by DuPont, and springs of a metal such as 300 series stainless steel. Once the design is finalized, the valve body and cylindrical slide may be injection molded or machined. Assembly of the final valve may be done with solvent welding, adhesive gluing, or ultrasonic welding.

Different balloon sizes require a different volumetric flow rate to achieve the desired scaffold inflation rate. By varying the size, number, or position of the holes in the cylindrical slide, different target volumetric flow rates could be achieved. Adjustment of these slide parameters to achieve the desired fluid flow rate for each balloon size allows the use of different cylindrical slides with the same valve body and spring. For example, a large balloon will allow a larger volumetric flow rate to achieve the target scaffold inflation rate. This might be achieved by simply making the though holes in the cylindrical slide larger.

A second set of inventive embodiments of a flow regulating valve for regulating flow of an inflation fluid to a balloon catheter includes a valve body enclosing a control chamber, a flexible restrictor membrane positioned within the control chamber, and a valve seat positioned within the control chamber distal to the membrane. The flexible restrictor membrane may be made of an elastomeric material. The control chamber includes a passageway for fluid flow. A proximal end of the valve body has a proximal flow orifice for connection with a catheter in fluid communication an inflation device. A distal end of the valve body has a distal flow orifice for connection with the balloon catheter.

The flexible restrictor membrane is positioned within the control chamber and includes an opening which allows fluid to flow distally or proximally through the membrane. The valve seat is positioned within the control chamber distal to the membrane and includes an opening for fluid to flow distally and proximally. The membrane and valve seat have surfaces transverse to the direction of fluid flow which include the openings.

The inflation fluid flows distally during balloon inflation and proximally during deflation. The membrane is operable to flex distally in response to fluid flow in the distal direction toward the valve seat during inflation of the balloon. As the membrane flexes toward the valve seat, restriction to fluid flow increases which controls the pressurization rate of the balloon to within a specified range.

The valve seat includes proximal and distal facing surfaces. Distal or proximal flow is allowed through the opening and around the valve seat. As distal flow flexes the membrane toward the valve seat, the restriction of flow around the valve seat increases. The opening in the valve seat can be axially aligned with the opening in the membrane. The alignment of the openings can allow the flow through the opening in the valve seat to be initially unrestricted by the flex of the membrane. When the flexing membrane comes into contact with the valve seat, the flow around the valve seat can be completely prevented.

An exemplary embodiment of this second set of embodiments of a flow regulator valve is shown in FIGS. 8-12.

Figure 8:
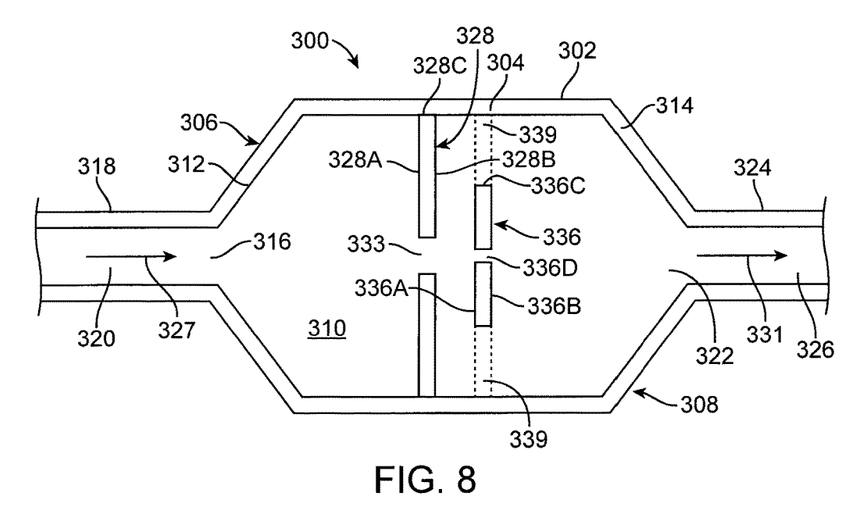
FIG. 8 depicts a flow regulating valve including a valve body, flexible membrane, and valve seat.

FIG. 8 depicts a longitudinal cross section of a valve 300 which includes a cylindrical valve body 302. Valve body 302 is formed of a cylindrical wall 304 and tapered proximal wall 312 and tapered distal wall 314. Walls 304, 312, and 314 enclose a control chamber 310 that includes a passage way between a proximal end 306 to a distal end 308 of valve 300.

Valve body 302 further includes a proximal orifice 316 in proximal wall 312 that is in fluid communication with a fluid source such as an indeflator (not shown). Valve body 302 is connected to a proximal catheter section 318 with an inflation lumen 320 that leads into proximal orifice 316.

At distal end 308, valve body 302 has a distal orifice 322 in distal wall 314 that is in fluid communication with a delivery balloon (not shown). Valve body 302 is connected to a distal catheter section 324 with an inflation lumen 326 that leads into distal orifice 322.

Valve 300 includes a flexible membrane 328 disposed at an axial position in the flow passageway formed by valve body 302. Membrane 328 is a sheet with a proximal surface 328A and distal surface 328B and an opening 333 that allows flow of fluid distally or proximally. An outer edge 328C of membrane 328 is attached to the inner surface of valve body 302. Membrane 328 has the shape of a disc with opening 333 at or near its center which coincides with the cylindrical axis of valve body 302. In the valve 300 shown in FIG. 8, all flow distally or proximally goes through opening 333.

Valve 300 further includes a valve seat 336 which is positioned at an axial position distal to membrane 328. Valve seat 336 has a proximal surface 336A and a distal surface 336B, an outer edges 336C and an opening 336D. Fluid can flow through opening 336D and around valve seat 336 through the spaces between outer edges 336C and inner surface of valve body 302.

Figure 9:
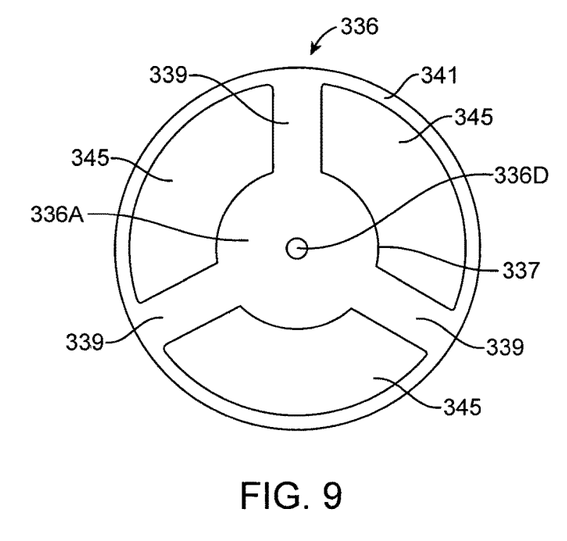
FIG. 9 depicts cross-sectional view of the valve seat of the valve in FIG. 8 from a proximal direction.

FIG. 9 depicts cross-sectional view of valve seat 336 from a proximal direction. As shown in FIG. 9, valve seat 336 includes disc 337 suspended in the control volume of valve body 302. Disc 337 is suspended by three radial arms 339 that extend radially outward to a ring 341 which is bonded to an inner surface of valve body 302 which fixes valve seat 336 in place. Fluid can flow around disc 337 through openings 345 formed by outer edges 328C of disc 337 and edges of arms 339 and ring 341.

During inflation, the inflation lumen is pressurized with inflation fluid and flows distally or from left to right in FIG. 8. Inflation fluid flows from proximal catheter section 318, as shown by arrow 327, into valve body 302 and out of valve body 302 through distal catheter section 324, as shown by arrow 331. FIG. 8 depicts a configuration with no fluid flow or a low flow rate since membrane 328 is not flexing.

Figure 10:
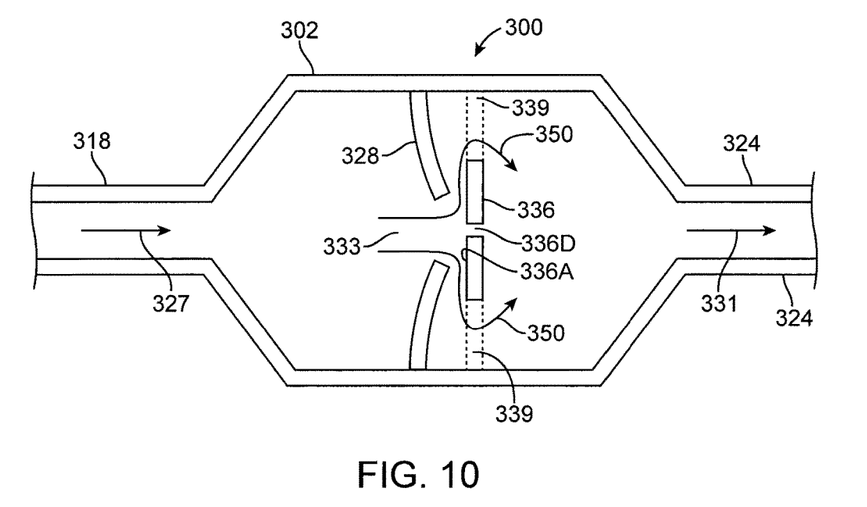
FIG. 10 depicts the valve of FIG. 8 in a configuration during inflation with the membrane flexed which partially restricts fluid flow.

FIG. 10 depicts valve 300 in a configuration during inflation in which the flow is sufficient to cause membrane 328 to flex which partially restricts fluid flow. As flow rate is increased, the application of pressure and the resulting flow causes membrane 328 to flex in a distal direction or to the right. Specifically, the central portion of membrane 328 surrounding opening 333 flexes to the right and moves towards valve seat 336. As membrane 328 moves towards valve seat 336, the gap between them becomes smaller, decreasing flow area, which increases restriction of fluid flow. As shown by arrows 350, fluid continues to flow around disc 337 of valve seat 336, however, the flow area has decreased due to flexing of membrane 328.

Figure 11:
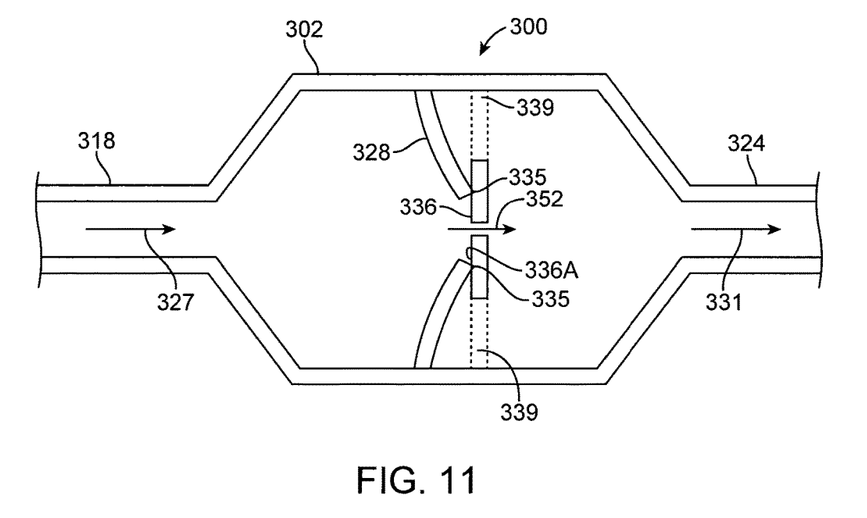
FIG. 11 depicts the valve of FIG. 8 in a configuration during inflation with the membrane flexed and sealed against the valve seat.

As the flow is increased further, membrane 328 completely engages or makes contact with proximal surface 336A of valve seat 336 and forms a seal against the surface. FIG. 11 depicts a configuration of valve 300 in which membrane 328 forms a seal 335 against valve seat 336. This configuration represents maximal restriction of flow. The sealing of membrane 328 against valve seat 336 prevents flow of fluid around disc 337 through openings 345. Flow only occurs through opening 336D of valve seat 336, as shown by arrow 352. Flow of fluid through opening 336D prevents valve 300 from completely "locking up." Opening 336D may be sized to only allow the desired inflation rate when the maximum inflation pressure is applied. This size would be determined during the valve design and would result in the targeted volumetric flow when a maximum conceivable pressure of, for example, 18 atm is applied to the valve.

Figure 12:
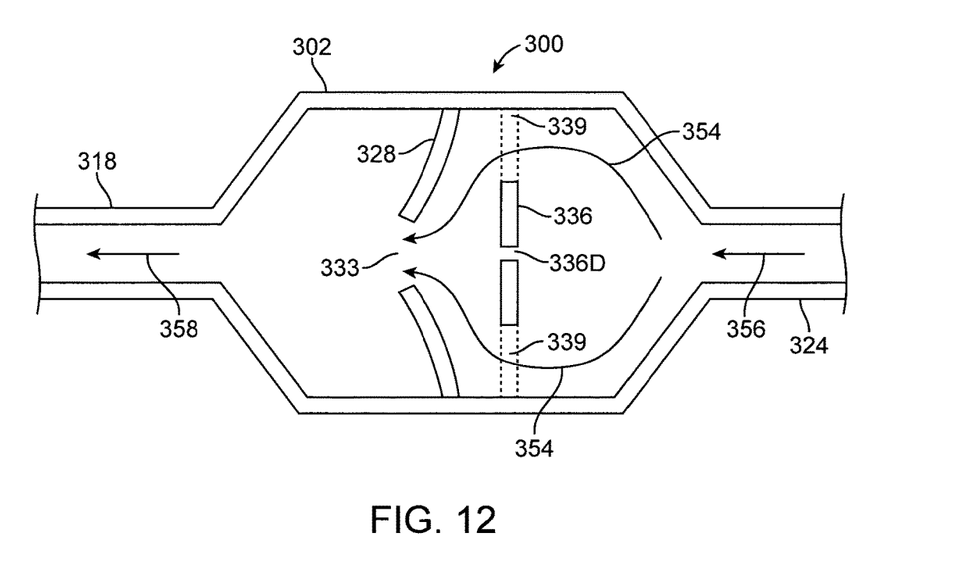
FIG. 12 depicts the valve of FIG. 8 during balloon deflation.

During balloon deflation, the fluid flows proximally or from right to left which causes the membrane to flex in the opposite direction, i.e., proximally or to the left. Thus, there is no increase in restriction of flow during deflation. FIG. 12 depicts configuration of valve 300 during balloon deflation. Fluid flows from distal catheter section 324 into valve body 302 as shown by arrow 356 and flows out of valve body 302 into proximal catheter section 318, as shown by arrow 358. Inside of valve body 302, fluid flows around valve seat 336 through openings 345 between arms 339, as shown by arrows 354 and through opening 333 in membrane 328. Membrane 328 is shown to flex proximally or to the left, however, there is no restriction to fluid flow.

Different balloon sizes require different flow rates to achieve the a desired or ideal inflation rate. The flow rate of valve 300 may be tuned by varying the size of disc 337 in valve seat 336. Another parameter to tune is the size of hole 333 in membrane 328. In this way, different valves may be easily configured for different size balloon catheters.

A variety of through hole designs in membrane 328 and configurations of passage ways in valve seat 336 are possible. This includes multiple holes in membrane 328 aligning with multiple passage ways in valve seat 336. The hole in membrane 328 may be circular or practically any other shape as long as this shape matches an appropriate passage way in the valve seat. Other potential designs include one in which a single hole is present in valve seat 336, but in membrane 328 is a single disc suspended by arms. In other words, the shapes of the through passage ways of the membrane and valve sheet as shown in FIG. 8, 9 are reversed.

Design of a valve 300 can be done by first building a prototype with a metal body, such as aluminum which allows for a variety of membranes and valve seats to be tested. Testing would be done with an apparatus which applies a known pressure of inflation fluid to the valve and measures the resulting flow rate. The goal is a flow rate versus pressure curve that is flat at the targeted flow rate.

Materials for the flexible membrane include elastomers such as silicone, thermoplastic polyurethane, C-Flex, thermoplastic polyester such as Hytrel, PEBAX, and other rubbers or elastomers.

The valve may be included as part of the final packaged product including the catheter, balloon, and stent. Therefore, the valve will be subjected to terminal sterilization that can include exposure to e-Beam radiation or ethylene oxide gas (ETO). Material properties of elastomers can be altered by e-beam sterilization, ETO, and by aging as well. This places additional requirements on the design and testing of the valve since the performance of a valve may change between manufacture of the valve and use of the valve during deployment of a scaffold in a patient.

As with the design of the first set of embodiments, valve 300 may be present in the catheter during manufacturing and testing. Additional designs for the cylindrical slide and valve seat of the first set are possible as there are other designs for the valve seat of the second embodiment utilizing a flexible membrane.

During the inflation process, the valve can be designed to start restriction of flow only when the pressure exceeds a specified maximum pressure. During an initial stage of the inflation process, the balloon pressure is not high enough to expand or significantly expand the scaffold. Thus, there is little or no risk of scaffold damage due to high inflation rate since the scaffold either is not being expanded or experience only slight expansion. Therefore, valves of the first and second sets of embodiments can be designed such that the restriction of flow does not start until the pressure exceeds a specified maximum pressure. Prior to reaching this specified maximum pressure, the pressurization rate can be higher than the maximum specified pressurization rate.

The maximum specified pressure may be about 2 atm, about 3 atm, about 4 atm, 2 to 4 atm, 2 to 3 atm, or 3 to 4 atm. During deployment below the maximum specified pressure, the pressurization rate can be up to 4 psi/sec, up to 6 psi/sec, up to 10 psi/sec, up to 20 psi/sec, about 30 psi/sec, 10 to 20 psi/sec, or 20 to 30 psi/sec. The pressurization rate below the maximum specified pressure may be entirely under the control of the operator of the inflation device.

The average pressurization rate between the maximum specified pressure and the maximum deployment pressure may be controlled to be about 4 psi/s, about 5 psi/s, about 6 psi/s, about 7 psi/s, about 8 psi/s, about 10 psi/s, 6 to 8 psi/s, 6 to 10 psi/s, 8 to 10 psi/s. The instantaneous pressurization rate may also be controlled to within these ranges.

The maximum deployment pressure can depend on the desired diameter of deployment. The maximum pressure may be about 7 atm, about 8 atm, about 10 atm, about 12 atm, about 14 atm, about 16 atm, about 18 atm, 7 to 8 atm, 8 to 10 atm, or 10 to 24 atm.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A flow regulator for regulating flow of an inflation fluid to a balloon catheter, comprising:
    a valve body enclosing a control chamber comprising a passageway for fluid flow, the valve body comprising a distal end and a proximal end, the distal end having a distal flow orifice for connection with the balloon catheter, the proximal end having a proximal flow orifice for connection with a catheter in fluid communication with an inflation device;
    a slidable restrictor body positioned within the control chamber, the restrictor body comprising a distal end and an opening formed through the distal end to allow fluid flow distally or proximally through the restrictor body; and
    a valve seat positioned distal to the restrictor body comprising a valve seat orifice which allows fluid to flow out of the distal flow orifice,
    wherein the slidable restrictor body is operable to slide distally from a starting position to a stopped position in response to fluid flow in the distal direction toward the valve seat during inflation of the balloon, wherein as the distal end of the restrictor body approaches the valve seat, the distal end of the restrictor body and the valve seat cooperate to increase restriction to fluid flow which controls pressurization rate of the balloon to within a specified range,
    wherein when the restrictor body slides distally from the starting position to the stopped position at which the distal end of the restrictor body contacts the valve seat, the distal end of the restrictor body blocks a first portion of the valve seat orifice and does not block a second portion of the valve seat orifice to allow fluid flow through the opening formed through the distal end of the restrictor body, into the second portion of the valve seat orifice, and out the distal flow orifice,
    wherein a second opening is formed through the distal end of the restrictor body, wherein when the restrictor body slides distally from the starting position to the stopped position at which the distal end of the restrictor body contacts the valve seat, the distal end of the restrictor body blocks the first portion of the valve seat orifice and does not block a third portion of the valve seat orifice to allow fluid flow through the second opening formed through the distal end of the restrictor body and into the third portion of the valve seat orifice, and
    wherein the opening and the second opening formed through the distal end of the restrictor body are equidistant from a center of the distal end of the restrictor body.

2. The flow regulator of claim 1, further comprising a biasing element that applies a biasing force that opposes the distal sliding of the restrictor body.

3. The flow regulator of claim 1, wherein the restriction of fluid flow is at a maximum when the distal end of the restrictor body contacts the valve seat.

4. The flow regulator of claim 1, wherein the slidable restrictor body is operable to slide proximally in response to fluid flow in the proximal direction during deflation of the balloon without increasing restriction of the proximal fluid flow.

5. The flow regulator of claim 1, wherein each of the valve body and slidable restrictor body has a cylindrical cross section.

6. The flow regulator of claim 1, wherein each of the valve body and slidable restrictor body has a square or rectangular cross section.

7. A flow regulator for regulating flow of an inflation fluid to a balloon catheter, comprising:
   a valve body enclosing a control chamber comprising a passageway for fluid flow;
   a distal end of the valve body with a distal flow orifice for connection with the balloon catheter,
   a proximal end of the valve body with a proximal flow orifice for connection with a catheter in fluid communication with an inflation device,
   a flexible restrictor membrane positioned within the control chamber comprising an opening which allows fluid to flow distally or proximally through the membrane;
   a valve seat positioned within the control chamber distal to the membrane comprising an opening for fluid to flow distally and proximally;
   wherein the membrane is operable to flex distally in response to fluid flow in the distal direction toward the valve seat during inflation of the balloon, wherein as the membrane flexes toward the valve seat restriction to fluid flow increases which controls pressurization rate of the balloon to within a specified range,
   wherein the valve seat comprises a plate fixed within a path of the fluid flow.

8. The flow regulator of claim 7, wherein the membrane and valve seat are positioned so that as the membrane flexes toward a proximal surface of the plate, restriction of flow around the valve seat increases.

9. The flow regulator of claim 7, wherein the flexing membrane is operable to engage a proximal surface of the plate, resulting in a maximum restriction of fluid flow.

10. The flow regulator of claim 7, wherein the membrane is operable to flex proximally away from a proximal surface of the plate in response to fluid flow in the proximal direction during deflation of the balloon without an increase in restriction of the proximal fluid flow.

11. A flow regulator for regulating flow of an inflation fluid to a balloon catheter, comprising:
    a valve body enclosing a control chamber comprising a passageway for fluid flow, the valve body comprising a distal end and a proximal end, the distal end having a distal flow orifice for connection with the balloon catheter, the proximal end having a proximal flow orifice for connection with a catheter in fluid communication with an inflation device;
    a slidable restrictor body positioned within the control chamber, the restrictor body comprising a distal end and an opening formed through the distal end to allow fluid flow distally or proximally through the restrictor body; and
    a valve seat positioned distal to the restrictor body comprising a valve seat orifice which allows fluid to flow out of the distal flow orifice,
    wherein the slidable restrictor body is operable to slide distally from a starting position to a stopped position in response to fluid flow in the distal direction toward the valve seat during inflation of the balloon, wherein as the distal end of the restrictor body approaches the valve seat, the distal end of the restrictor body and the valve seat cooperate to increase restriction to fluid flow which controls pressurization rate of the balloon to within a specified range,
    wherein when the restrictor body slides distally from the starting position to the stopped position at which the distal end of the restrictor body contacts the valve seat, the distal end of the restrictor body blocks a first portion of the valve seat orifice and does not block a second portion of the valve seat orifice to allow fluid flow through the opening formed through the distal end of the restrictor body, into the second portion of the valve seat orifice, and out the distal flow orifice,
    wherein a second opening is formed through the distal end of the restrictor body, wherein when the restrictor body slides distally from the starting position to the stopped position at which the distal end of the restrictor body contacts the valve seat, the distal end of the restrictor body blocks the first portion of the valve seat orifice and does not block a third portion of the valve seat orifice to allow fluid flow through the second opening formed through the distal end of the restrictor body and into the third portion of the valve seat orifice, and
    wherein a section of the distal end of the restrictor body is disposed between the opening and the second opening formed through the distal end of the restrictor body, wherein when the restrictor body slides distally from the starting position to the stopped position at which the distal end of the restrictor body contacts the valve seat, the section of the distal end of the restrictor body blocks the first portion of the valve seat orifice and does not block the second and third portions of the valve seat orifice.

* * * * *